United States Patent
Palti-Wasserman

(10) Patent No.: US 11,723,566 B2
(45) Date of Patent: Aug. 15, 2023

(54) DECEPTION DETECTION SYSTEM AND METHOD

(71) Applicant: Eye-Minders Ltd., Haifa (IL)

(72) Inventor: Daphna Palti-Wasserman, Haifa (IL)

(73) Assignee: Eye-Minders Ltd., Haifa (IL)

( * ) Notice: Subject to any disclaimer, the term of this patent is extended or adjusted under 35 U.S.C. 154(b) by 709 days.

(21) Appl. No.: 16/610,626

(22) PCT Filed: May 8, 2018

(86) PCT No.: PCT/IL2018/050504
§ 371 (c)(1),
(2) Date: Nov. 4, 2019

(87) PCT Pub. No.: WO2018/207183
PCT Pub. Date: Nov. 15, 2018

(65) Prior Publication Data
US 2020/0060598 A1  Feb. 27, 2020

Related U.S. Application Data

(60) Provisional application No. 62/503,578, filed on May 9, 2017.

(51) Int. Cl.
*A61B 5/16* (2006.01)
*A61B 3/113* (2006.01)
(Continued)

(52) U.S. Cl.
CPC .............. *A61B 5/164* (2013.01); *A61B 3/113* (2013.01); *A61B 5/0533* (2013.01); *A61B 5/163* (2017.08); *G06V 40/193* (2022.01)

(58) Field of Classification Search
CPC ........... A61B 5/164; A61B 5/163; A61B 5/16; A61B 3/113; A61B 3/00; A61B 5/0533; G06V 40/193
See application file for complete search history.

(56) References Cited

U.S. PATENT DOCUMENTS

2009/0216092 A1*  8/2009  Waldorf ................. A61B 5/164
                                                    600/301
2010/0009325 A1*  1/2010  Afanasiev .............. G09B 19/00
                                                    434/236

(Continued)

OTHER PUBLICATIONS

Labibah et al., Lie Detector with the Analysis of the Change of Diameter Pupil and the Eye Movement Use Method Gabor Wavelet Transform and Decision Tree, 2018 IEEE International Conference on Internet of Things and Intelligence System (IOTAIS), pp. 214-220 (2018) (Year: 2018).*

(Continued)

*Primary Examiner* — Namrata Boveja
*Assistant Examiner* — Divesh Patel
(74) *Attorney, Agent, or Firm* — Potomac Law Group, PLLC

(57) ABSTRACT

There is provided herein a computer implemented method for identifying if a subject is being deceptive, the method comprising: exposing a subject to a stimuli sequence and to a visual task; receiving from one or more sensors temporal data, indicative of the dynamics of at least one eye of a subject, wherein the received data comprises responsive and non-responsive data, the responsive data is responsive to the visual task; synchronizing the stimuli sequence with the received temporal data; analyzing the temporal data, which is indicative of the dynamics of the at least one eye of a subject; determining a probability of the subject being deceptive based on the analysis; and producing an output signal indicative of the probability of the subject being deceptive.

20 Claims, 7 Drawing Sheets

(51) Int. Cl.
*A61B 5/0533* (2021.01)
*G06V 40/18* (2022.01)

(56) References Cited

U.S. PATENT DOCUMENTS

| | | | | |
|---|---|---|---|---|
| 2010/0324454 | A1* | 12/2010 | Kircher | A61B 5/164 |
| | | | | 600/587 |
| 2011/0043759 | A1* | 2/2011 | Bushinsky | A61B 5/163 |
| | | | | 351/210 |
| 2011/0109879 | A1 | 5/2011 | Palti-Wasserman | |
| 2015/0294149 | A1 | 10/2015 | Palti-Wasserman | |
| 2015/0355815 | A1 | 12/2015 | Palti-Wasserman | |
| 2016/0128568 | A1* | 5/2016 | Bellamy | A61B 3/005 |
| | | | | 351/209 |
| 2016/0335483 | A1* | 11/2016 | Pfursich | G06V 10/40 |
| 2017/0119296 | A1 | 5/2017 | Macknik et al. | |

OTHER PUBLICATIONS

International Search Report and Written Opinion issued in application No. PCT/IL2018/050504 dated Jun. 27, 2018.

* cited by examiner

DECEPTION DETECTION SYSTEM AND METHOD

TECHNICAL FIELD

The present disclosure relates generally to deception detection.

BACKGROUND

Lying is a complex task, which involves both mental effort and emotional impact from a person. Its influence and self-expression on different people in different situations varies significantly. While lying, a person may experience stress, anger, fear, and other emotions, as well as cognitive load associated with the task of lying, increased concentration associated with being uncooperative and trying not to get caught or other mental efforts. He may experience one of these signs or several. However, not only liars experience these signs. Some of these signs may be experienced by truth telling people under investigation conditions. In addition, some of these signs may be experienced by a person, who is not lying and is stressed for other reasons. These are some of the reasons that it is difficult to identify liars based on mental effort and emotional impact.

The polygraph, popularly referred to as a lie detector, measures physiological indicators of stress, which is an indicator of lying. When a person lies, he experiences typical autonomic reactions, triggered by stress. These autonomic reactions such as: an increase in skin conductivity, heart rate, respiration rate and blood pressure, capillary dilation, and muscular movement, are not easily controlled by the conscious mind. The polygraph detects these autonomic reactions. However, these measures which are supposed to indicate a short-term stress response from lying can result from other reasons associated with mental effort and emotional states such as: fear, anger, familiarity, significance to the subject, and surprise, for example. Accordingly, this decreases the capability of a polygraph to detect liars with high sensitivity and specificity. In addition, there are many issues with polygraph tests because many people have found ways to cheat the system. Some people have been known to take sedatives to reduce anxiety, use antiperspirant to prevent sweating and position pins or biting parts of the mouth after each question to demonstrate a constant physiological response.

The polygraph was invented in 1921, and is currently considered the gold standard for lie detection, although it has many limitations and is considered unreliable. Among its limitations, it is intrusive, requires an expert examiner, can be fooled, and cannot be used for screening crowds (takes hours for a single test) or for working in the field. Alternative technologies like Functional Magnetic Resonance Imaging and Thermal Scanners are still in very early stages of research. In recent years, some research has been done on eye-based lie detection, however most of it is academic.

The human visual system includes a combination of peripheral-vision and centric-vision. Peripheral-vision provides a wide-angle view of the world using the retina to catch light. It is very sensitive to motion and to low light but has a low resolution. Centric-vision, on the other hand, provides a small window to the world using the fovea (radius only 0.5 mm). It has low sensitivity, but high resolution, thus it provides a detailed view in a small window only in bright light. Accordingly, people must move their eyes (eye movements) continuously to get an optimal view of the world.

Eye movements are a combination of both voluntary and involuntary movements. The eye movement repertoire includes many types of movement: fixation, gaze, saccades, convergence, rolling, smooth-pursuit, nystagmus, drift, micro saccades, and physiological nystagmus. Some of these eye movements are very fast, even ballistic (Saccades 900°/s), and some are much slower (smooth pursuit at 30°/s). Some eye movements require a visual stimulus to stimulate them, others do not. Different stimuli evoke different types of eye movements. Today eye movements are usually acquired by using optic sensors such as video cameras, line scanners and photo-diodes.

A person's eye movements are complex signals, which are influenced by many factors: the presented stimulus, the environment (where the measurement takes place), different attributes of the person and the person's current status. Thus, eye movements are rich signals which hold a lot of changing and permanent information on the person behind them. Eye movements may reflect and quantify, among other things, a person's: cognitive state, cognitive load, neuropsychological status, neurophysiological status, eye anatomy, illness, injury, drunkenness, intoxication, current state of mind/emotions (stress, fatigue, excitement, fear, surprise, anger, familiarity/affection) and personal characteristics. All of this information on a person exists simultaneously in a person's eye movement signals, and accordingly differences within and between people's eye-movements exist.

In today's difficult times, terrorism, crime and deception are unfortunately a daily concern of citizens of most countries around the globe. It has many faces: cybercrime, suicide bombers, airplane hijacking, murder, theft, fraud, embezzlement, industrial espionage, etc. A "good and effective" lie-detector can provide an important tool for fighting all of these concerns. Lie detection technologies are applicable to a dual market: the security/government market (HLS, TSA, military, law enforcement, security agencies, government) and the private sector (investigators, lawyers, technology & business companies, health care, insurance, banks, trade floors, and more).

Lie detection tools are used as a dual tool for investigation and for screening. As a screening tool, lie detection technologies can be used for pre-employment for candidates and periodic credibility checks for employees in both markets (security/government and private). In addition, a lie detector which will be capable of high throughput screening could be very beneficial in screening crowds at boarders and airports for counter terrorism or as aid to customs routine checks.

There is still a need in the art for reliable, effective and efficient deception detection systems and methods.

SUMMARY

Aspects of the disclosure, according to some embodiments thereof, relate to systems and methods for deception detection. More specifically, but not exclusively, aspects of the disclosure, according to some embodiments thereof, relate to systems and methods for deception detection based on eye dynamics.

According to some embodiments, the systems and methods disclosed herein, improve the deception detection performance and are beneficial for both client and testee (tested subject). For the testee the technology provides a shorter, contactless, less invasive and less stressful investigation with a sense of more privacy and increased reliability. For the client, the technology provides a test, which does not require a professional examiner, has a fast and simple set-up time (e.g., minutes), is portable (small foot print), can work in a variety of environments (indoors and in the field), has high throughput (e.g., minutes for a testee instead of hours), high performance (including anti counter-measures), reliability (measures both stress and cognitive load) and a lower price tag.

According to some embodiments, the terms "deceptive", "deceiving" and "deception" may refer to lying, cheating, concealing information, ignoring, being at least partially uncooperative, being manipulative, or any combination thereof. These terms may be used interchangeably.

According to some embodiments, the systems and methods to detect liars are based on their eyes. According to some embodiments, the systems and methods disclosed herein are based on an analysis of the dynamic characteristics, behaviors, changes and variations of the eyes, referred to as Eye-Dynamic, and not on static information of the eyes (eye location-gaze for example). Accordingly, the systems and methods are focused on accurately acquiring, enhancing and preserving the Eye-Dynamic, and then analyzing and fusing it into meaningful information to be used to detect liars.

According to some embodiments, the deception detection systems and methods use a specially designed deception-detection Eye-Session that includes algorithms and protocols, which have been developed for the task of detecting liars by their eyes.

According to some embodiments, the systems and methods disclosed herein may provide a dual tool for both screening and investigation for dual markets (security/government and private sector). The advantages and unique SPEC (Specification) of the systems and methods disclosed herein in accordance with some embodiments, position it as an improved alternative to the polygraph, and as an enabling technology for new applications, where no other technology is available.

According to some embodiments, there is provided herein a computer implemented method for identifying if a subject is being deceptive, the method comprising: exposing a subject to a stimuli sequence and to a visual-task; receiving from one or more sensors temporal data, indicative of the dynamics of at least one eye of a subject, wherein the received data comprises responsive and non-responsive data, the responsive data is responsive to the visual-task; synchronizing the stimuli sequence with the received temporal data; analyzing the temporal data, which is indicative of the dynamics of the at least one eye of a subject; determining a probability of the subject being deceptive based on the analysis; and producing an output signal indicative of the probability of the subject being deceptive.

According to some embodiments, there is further provided herein an electronic device comprising one or more processors; and memory coupled to the one or more processors, the memory storing one or more programs configured to be executed by the one or more processors, the one or more programs including instructions for: exposing a subject to a stimuli sequence and to a visual-task; receiving from one or more sensors temporal data, indicative of the dynamics of at least one eye of a subject, wherein the received data comprises responsive and non-responsive data, the responsive data is responsive to the visual-task; synchronizing the stimuli sequence with the received temporal data; analyzing the temporal data, which is indicative of the dynamics of the at least one eye of a subject; determining a probability of the subject being deceptive based on the analysis; and producing an output signal indicative of the probability of the subject being deceptive.

According to some embodiments, there is further provided herein an electronic device for identifying if a subject is being deceptive, the electronic device comprising one or more processors; and memory coupled to the one or more processors, the memory storing one or more programs configured to be executed by the one or more processors, the one or more programs including instructions for: exposing a subject to a stimuli sequence and to a visual-task; receiving from one or more sensors temporal data, indicative of the dynamics of at least one eye of a subject, wherein the received data comprises responsive and non-responsive data, the responsive data is responsive to the visual-task; synchronizing the stimuli sequence with the received temporal data; analyzing the temporal data, which is indicative of the dynamics of the at least one eye of a subject; determining a probability of the subject being deceptive based on the analysis; and producing an output signal indicative of the probability of the subject being deceptive.

According to some embodiments, analyzing the temporal data may further include the step of identifying responsive and non-responsive dynamics in (the analyzed) temporal data.

According to some embodiments, the method/instructions may further include the step of acquiring, using the one or more sensors, the temporal data indicative of the dynamics of the at least one eye of a subject.

According to some embodiments, the method/instructions may further include calculating from the received temporal data at least one eye-dynamic signal.

According to some embodiments, the method/instructions may further include extracting one or more parameters from the one or more eye-dynamic signals. The one or more parameters from the one or more eye-dynamic signals may indicate the mental effort and/or the emotional state of subject.

According to some embodiments, the method/instructions may further include applying one or more counter measure algorithms using the at least one eye-dynamic signal to detect deception.

According to some embodiments, the method/instructions may further include applying one or more fusion algorithms to the at least one eye-dynamic signals, to calculate the probability of the subject being deceptive.

According to some embodiments, there is further provided herein a non-transitory computer-readable storage medium storing one or more programs, the one or more programs comprising instructions which, when executed by an electronic device, cause the electronic device to implement the method(s) disclosed herein.

According to some embodiments, there is further provided herein a system for identifying if a subject is being deceptive, the system comprising: one or more processors comprising: a visual task module configured to produce a visual task to be presented to the subject; a stimuli sequence module configured to produce a stimuli sequence to be presented to the subject; an input module configured to receive from one or more sensors temporal data, indicative of the dynamics of at least the one eye of a subject, wherein the received data comprises responsive and non-responsive data, the responsive data is responsive to the visual task; a synchronizing module configured to synchronize the stimuli sequence with the received temporal data; an eye-dynamics processing module configured to analyze the temporal data, which is indicative of the dynamics of the at least one eye of a subject and to determine a probability of the subject being deceptive based on the analysis; and an output module configured to produce an output signal indicative of the probability of the subject being deceptive; and one or more sensors configured to acquire measurements relating to the dynamics of the at least one eye of a subject.

According to some embodiments, there is further provided herein a system for identifying if a subject is being deceptive, the system comprising: one or more processors comprising: a visual task module configured to produce a visual-task to be presented to the subject; a stimuli sequence module configured to produce a stimuli sequence to be presented to the subject; an eye dynamics processing module configured to: receive from one or more sensors temporal data, indicative of the dynamics of at least one eye of a subject, wherein the received data comprises responsive and non-responsive data, the responsive data is responsive to the visual-task, and analyze the temporal data, which is indicative of the dynamics of the at least one eye of a subject and to determine a probability of the subject being deceptive based on the analysis; a synchronizing module configured to synchronize the stimuli sequence with the received temporal data; and an output module configured to produce an output signal indicative of the probability of the subject being deceptive; and a display configured to expose the subject to the visual-task.

According to some embodiments, the system may further include one or more sensors configured to acquire measurements relating to the dynamics of the at least one eye of a subject. the sensor comprises a camera, an electrode, a photodiode, an ultrasonic sensor, an Ober sensor, a magnetic sensor, or any combination thereof.

According to some embodiments, the display may further be configured to expose the subject to the stimuli sequence.

According to some embodiments, the system may further include a stimuli-providing member configured to expose the subject to the stimuli sequence.

According to some embodiments, the eye dynamics processing module is further configured to calculate from the received temporal data at least one eye-dynamic signal. The eye dynamics processing module may further be configured to extract one or more parameters from the one or more eye-dynamic signals. The one or more parameters from the one or more eye-dynamic signals may indicate the mental effort and/or the emotional state of a subject. The eye dynamics processing module may further be configured to apply one or more counter measure algorithms using the at least one eye-dynamic signal to detect deception. The eye dynamics processing module may further be configured to apply one or more fusion algorithms to the at least one eye-dynamic signals, to calculate the probability of the subject being deceptive.

According to some embodiments, the visual task may be imbedded with the stimuli sequence.

According to some embodiments, the subject may further be exposed to a relaxing element (for example but not limited to within the visual task).

According to some embodiments, the stimuli-sequence may include at least one evoking-stimulus.

According to some embodiments, the stimuli-sequence may include two or more stimuli, including at least one evoking stimulus, at least one neutral stimulus, at least one intermediate stimulus or any combination thereof.

According to some embodiments, an optimal timing for exposing the subject to a stimulus from the stimuli sequence may be determined based on physiological activity and/or behavior indicators of the subject. The physiological activity of the subject may include, for example, eye-dynamics, GSR, heart-rate, respiration, body temperature, blood pressure or any combination thereof.

According to some embodiments, the stimuli-sequence may include a visual stimulus, an auditory stimulus, a tactile stimulus or any combination thereof.

Certain embodiments of the present disclosure may include some, all, or none of the above advantages. One or more other technical advantages may be readily apparent to those skilled in the art from the figures, descriptions, and claims included herein. Moreover, while specific advantages have been enumerated above, various embodiments may include all, some, or none of the enumerated advantages.

Unless otherwise defined, all technical and scientific terms used herein have the same meaning as commonly understood by one of ordinary skill in the art to which this disclosure pertains. In case of conflict, the patent specification, including definitions, governs. As used herein, the indefinite articles "a" and "an" mean "at least one" or "one or more" unless the context clearly dictates otherwise.

BRIEF DESCRIPTION OF THE FIGURES

Some embodiments of the disclosure are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the disclosure. For the sake of clarity, some objects depicted in the figures are not to scale.

In the Figures.

DETAILED DESCRIPTION

Figure 1:
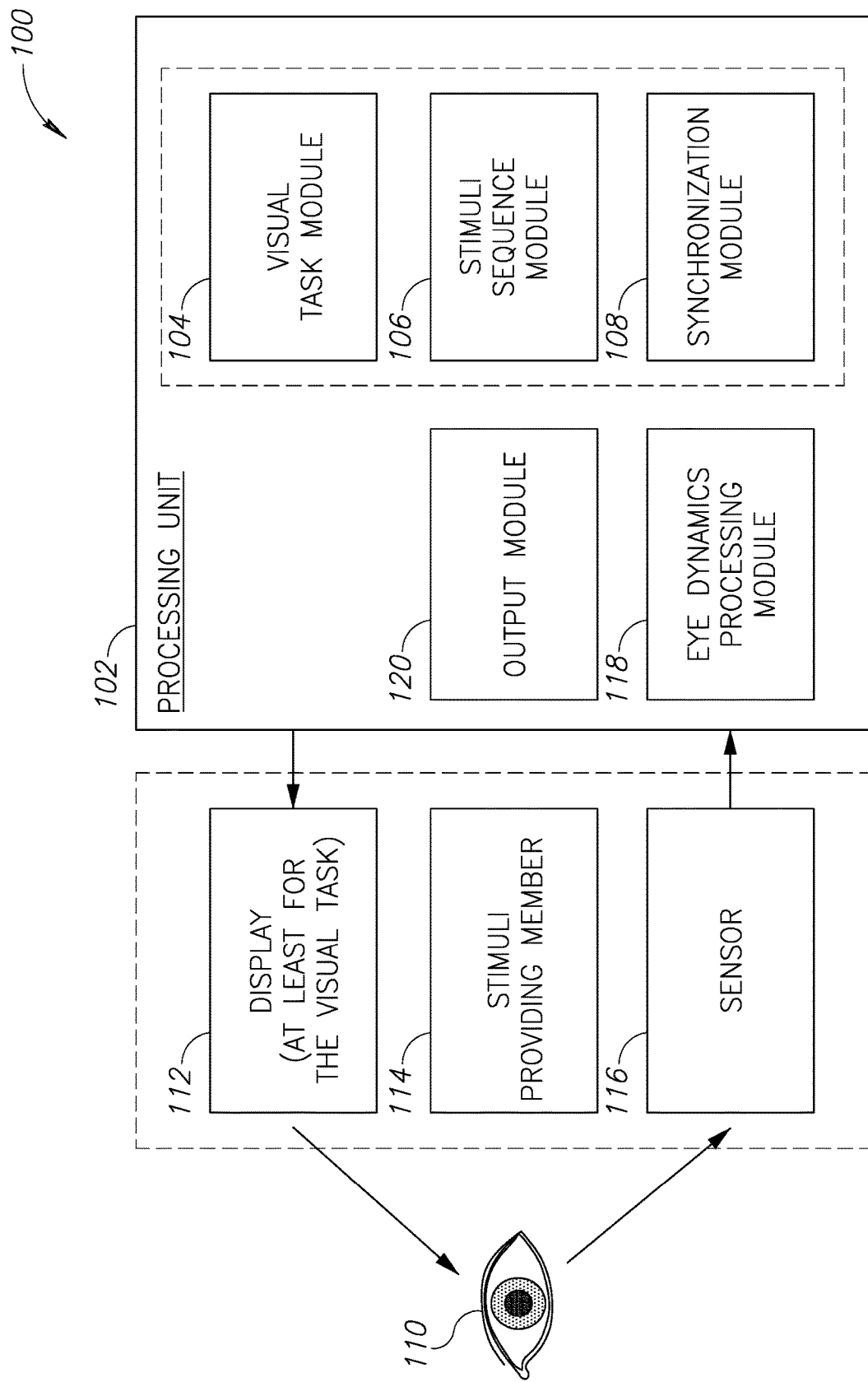
FIG. 1 schematically depicts a block diagram of a system, according to some embodiments.

The principles, uses and implementations of the teachings herein may be better understood with reference to the accompanying description and figures. Upon perusal of the description and figures present herein, one skilled in the art will be able to implement the teachings herein without undue effort or experimentation. In the figures, same reference numerals refer to same parts throughout.

There is provided herein, in accordance with some embodiments, a system and method for detecting, using an "eye session", liars, or in general, people who are not telling the truth or the whole truth, people that are concealing some information, being uncooperative, manipulative, deceptive, or the like. According to some embodiments, the eye-session is focused on accurately acquiring, enhancing and/or preserving the eye signal characteristics and dynamics of the eyes, which can be referred to as Eye-Dynamics. The information the Eye-Dynamics is then analyzed and used to detect liars. One of the advantages of the system, according to some embodiments, is that it may be automatic and does not require an expert investigator.

Reference is now made to FIG. 1, which schematically depicts a block diagram of a system, according to some embodiments. Deception detection system 100 include a processing unit 102 (which may include one or more processors). Processing unit 102 includes a visual task module 104 configured to provide a visual task to a subject (testee—the person being investigated, tested, checked or screened) 110, a stimuli sequence module 106 configured to provide a stimuli sequence to subject (testee) 110 and a synchronization module 108 configured to synchronize between visual task module 104, a sensor 116 and stimuli sequence module 106.

The visual task(s) provided by visual task module 104 is presented to subject (testee) 110 on display 112, and the stimuli sequence provided by stimuli sequence module 106 to subject (testee) 110 by a stimulus providing member 114 or by display 112.

It is noted that, in accordance with some embodiments, a visual task module (such as visual task module 104) and a stimuli sequence module (such as stimuli sequence module 106) may be joint, i.e., one module, that provides both the visual tasks and the stimuli sequence.

The eye response of subject (testee) 110 to the visual task and the stimuli sequence is collected by sensor 116 (which may include more than one sensor) and transferred to processing unit 102 or particularly to eye dynamics processing module 118 for processing of the eye dynamics of subject (testee) 110. Information/data/signal(s)/analysis of the eye dynamics and indication of the probability of the subject being deceptive are provided by an output module 120 and optionally presented on display 112 or on another display.

It is noted that, in accordance with some embodiments, processing unit 102 or any of the modules thereof, may be separated from the test location. For example, display 112, stimuli providing member 114 and/or sensor 116 may be located at a site where testee 110 is tested, while processing unit 102 or any of the modules thereof, may be located at a remote location, e.g on a remote server, cloud, block chain server or any other site.

Figure 2:
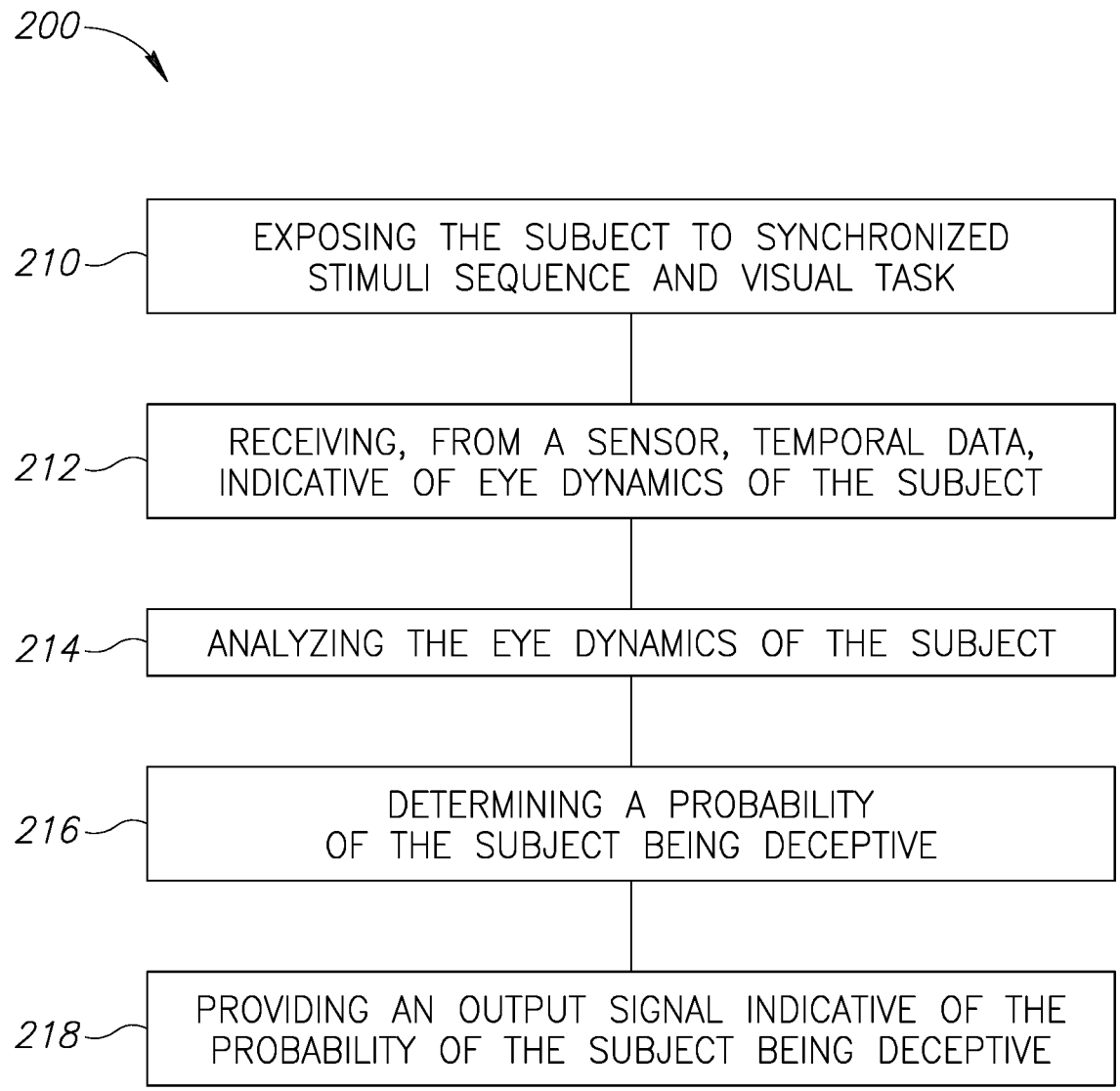
FIG. 2 schematically depicts a flow chart of a method, according to some embodiments.

Reference is now made to FIG. 2, which schematically depicts a flow chart 200 of a method for determining the probability of a subject being deceptive, according to some embodiments:

Step 210 includes exposing the subject (testee) to synchronized stimuli sequence and a visual task. According to some embodiments, the stimuli sequence is a part of or embedded in the visual task.

Step 212 includes receiving, from a sensor, synchronized temporal data, indicative of eye-dynamics of the subject.

Step 214 includes analyzing the eye-dynamics of the subject.

Step 216 includes determining a probability of the subject being deceptive.

Step 218 includes providing an output signal indicative of the probability of the subject being deceptive.

Figure 3:
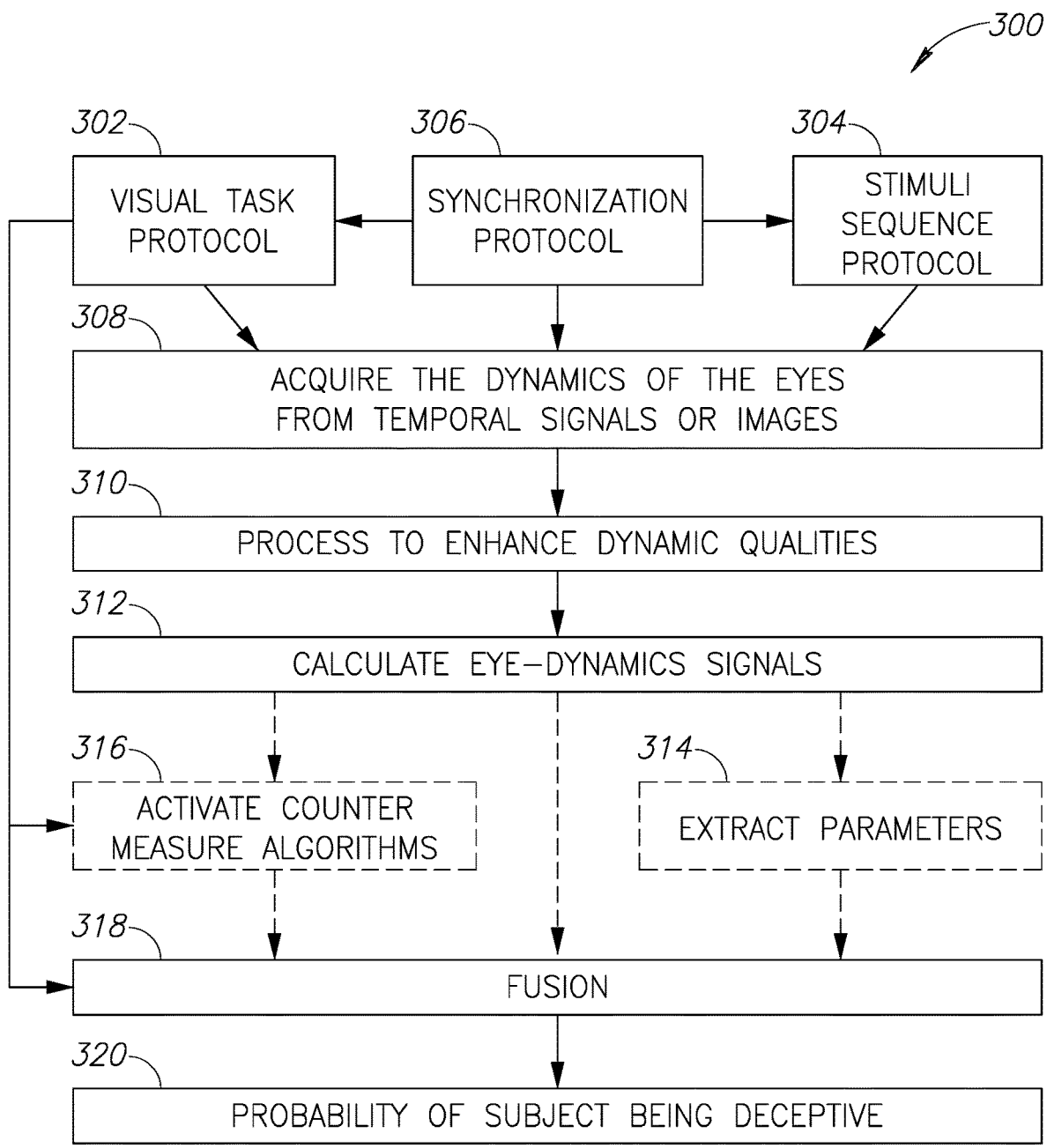
FIG. 3 schematically depicts a flow chart of a method, according to some embodiments.

Reference is now made to FIG. 3, which schematically depicts a flow chart 300 of a method for determining the probability of a subject being deceptive, according to some embodiments:

Providing the subject (testee) with a visual task according to a visual task protocol 302 and a stimuli sequence according to a stimuli sequence protocol 304, such that the visual task, the stimuli-sequence and the acquisition of dynamics of the eyes 308 are all synchronized according to a synchronization protocol 306.

The dynamics of the eye(s) of the tested subject are acquired from temporal signals or images 308 provided by one or more sensors and, if needed, processed to enhance dynamic qualities 310 e.g, enhance image quality, reduce noise such as head movements etc.

Eye dynamics signal(s) indicative of dynamic eye characteristics are then calculated/computed/analyzed 312. Relevant parameters may be extracted from the eye-dynamic signal(s) 314, and counter-measure algorithms may be activated 316 on the eye-dynamic signals. A fusion process 318 may be applied on the eye-dynamic signals, extracted parameters and the output from counter-measure algorithms to obtain an output which provides probability of subject being deceptive (320).

Deployment Platforms

A system based on the technology, as disclosed herein according to some embodiments, may be deployed in a variety of different platforms. It may be used in new stand-alone products (examples: table-top unit, independent post), deployed in existing products (examples: polygraph, goggles, glasses, mobile device), and be used as an add-on to existing products (examples: add-on for PC/laptop/polygraph/mobile devices). The platform selection may be effected by many factors such as: type of use (screening or investigation tool), target market (security, government, industry, enterprise, private sector, etc.), environmental conditions, portability requirements, throughput requirements, and designated application. Any selected platforms may be autonomic or may communicate with an outside source such as a server or a cloud database.

In some embodiments, the technology is deployed in a platform based on goggles or smart glasses, which are often used for virtual reality or augmented reality applications. In these embodiments, the acquisition of the eye-dynamic response signal may be acquired from both eyes or just from one eye, and the visual-task and visual stimuli (if used), may be presented to both eyes or just to one. In some embodiments, where acquisition is done from one eye, the visual-task and visual stimuli (if used) may be presented in the other eye. Thus, in this embodiment, the display will be visible only to one of the eyes, and the acquisition hardware will obtain the eye-response from the other eye.

In some embodiments, the system is designed as a stand-alone unit. Thus, hardware, software and components (sensors, illumination, microphone, speakers, display, controller, etc.) may be integrated into the unit. In some embodiments, the unit is designed to be placed on a table, and the testee will sit on a chair in front of the unit. In other embodiments, the unit is designed as a standing post, and the testee is investigated, while he is standing in front of the unit.

Figure 4:
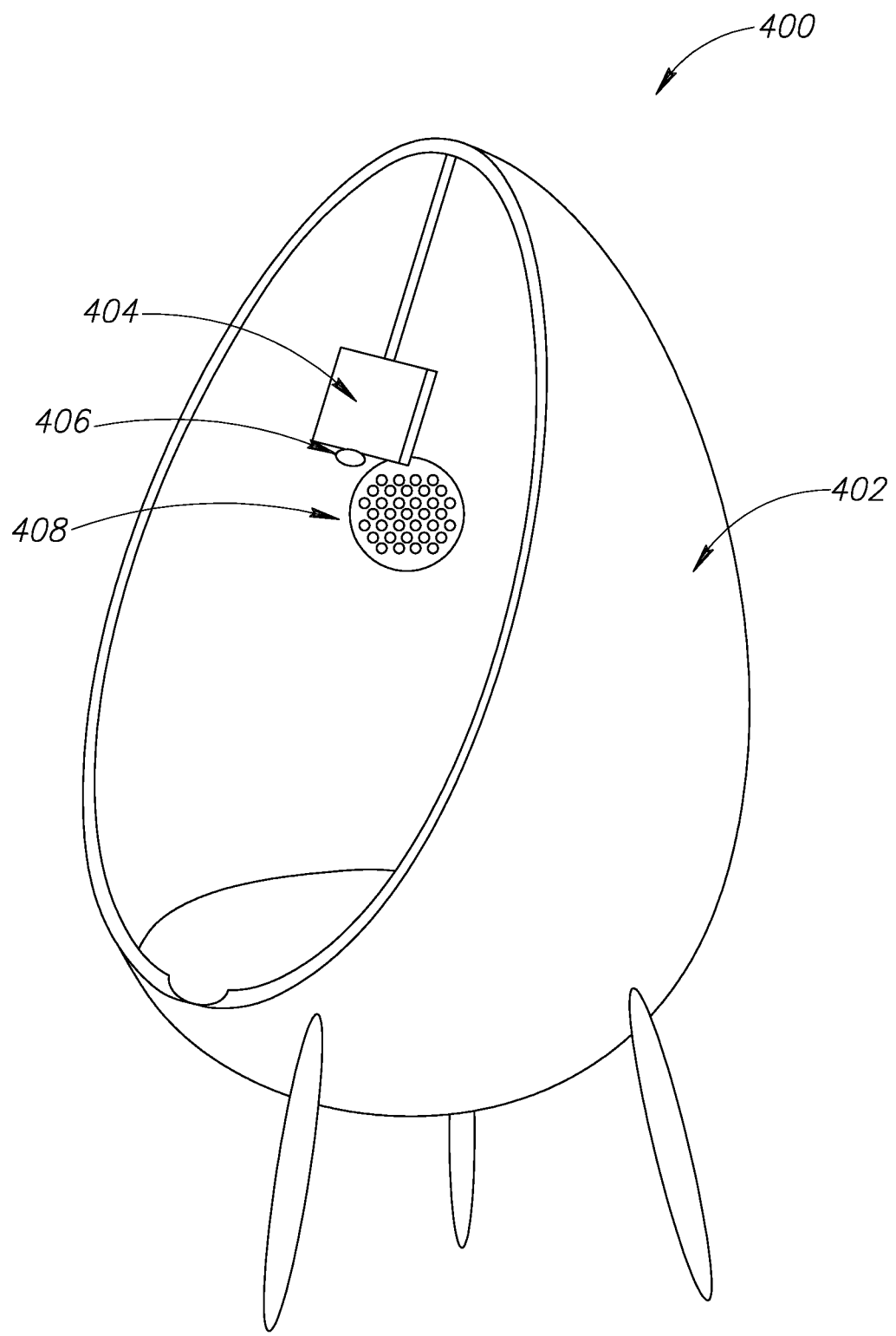
FIG. 4 schematically depicts an example of a system design, according to some embodiments.

In some embodiments, the system components may be integrated in a selected environment. For example, as shown in FIG. 4, the system 400 components may be integrated in a specially designed, fully inclusive sitting post. In this embodiment, the testee sits comfortably, thus his posture, position and eyes location are fixed during the investigation. In some embodiments, the sitting post 402 may be shaped as a semi closed environment, thus in addition to all components (such as screen 404, camera 406 and speaker 408) may be integrated in the post and the testee comfortably seated, is shielded from the environment (ambient light, noise, distractions etc.).

In other embodiments, the selected environment may be an entire room, used specifically for investigation. In some "room embodiments", when it is required that the testee is investigated without the testee's knowledge that the current deception-detection technology is used, multiple cameras that can acquire the testee's eye-response from a distance are used.

In some embodiments, mobiles are used as a platform for the system. In these embodiments, the mobile's components: processing unit, WiFi, Blue-Tooth, internet, camera, illumination, screen, speakers and microphone, may be used in conjunction with a deception detection application downloaded to the mobile device. In some embodiments, the mobile unit may communicate with additional units such as, but not limited to: a server, a cloud data-base, a local PC, another mobile device, a local data-base, etc. In some embodiments, if required, additional components are added to the mobile, as an add-on, to enhance its performance. For example, a "skin" which includes a camera, a processing unit or illumination, or any combination of these elements, may be added to a mobile phone or tablet.

Eye Dynamics

The technology (system and method), disclosed herein in accordance with some embodiments, is based on the dynamic characteristics, behaviors, changes and/or variations of the eyes, which may be referred to as Eye-Dynamic, and not on static information of the eyes (eye location-gaze for example).

Most existing eye-based technologies and application are based on "classical eye-tracking". They include the acquisition, tracking and analysis of where a person is looking. This is usually referred to as eye-movements and gaze. When working with eye-movements and gaze, the main goal of the acquisition hardware and algorithms is to extract the exact location of the eyes. Thus, the exact 3D real world coordinates of where a person is looking are calculated from the acquired eye signal. To get an accurate position of the eyes, different post-processing algorithms are used on the acquired signals. These algorithms improve the accuracy of the eye position, but the trade-off is losing other information, which the signals may include. In addition, this approach requires calibration, and often recalibration of the system to obtain the exact location of the eye.

Figure 5B:
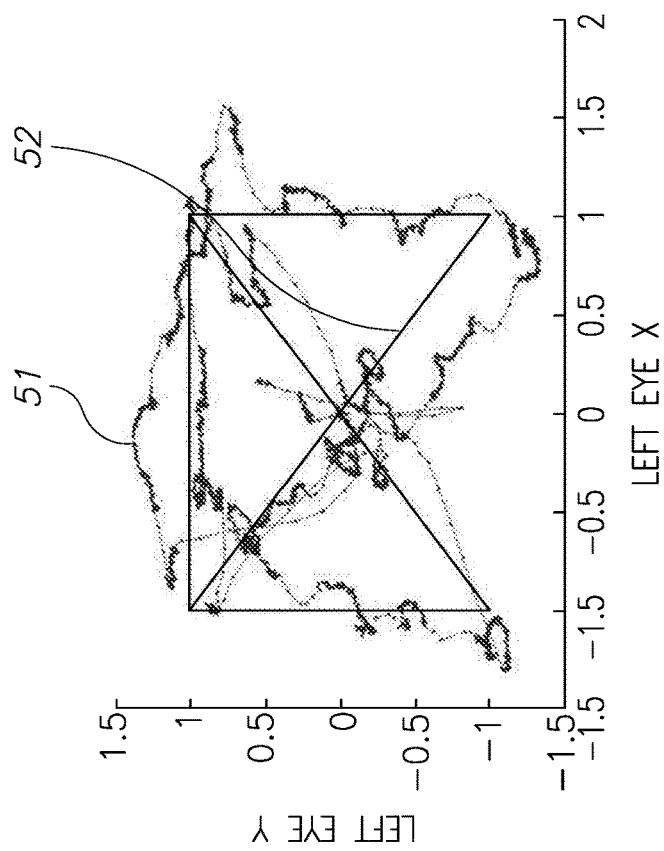
FIGS. 5A and B depict two examples of the trajectory of a moving target and the corresponding eye-movements, according to some embodiments.
Figure 5A:
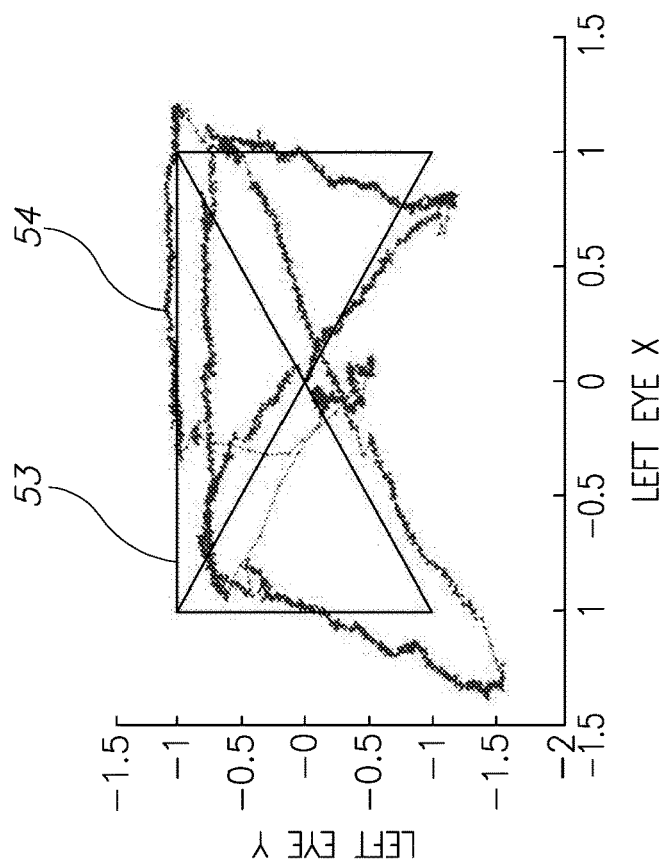

The system and method disclosed herein in accordance with some embodiments, unlike the existing eye-based technologies described hereinabove, are based on the dynamics, characteristics, behaviors, changes and/or variations of the eyes referred to as eye-dynamic. The eye-dynamics signals may include, in accordance with some embodiments, any-of or any combination of the following: pupil dilation dynamics, blinking dynamics and eye-path dynamics (path/trajectory not coordinates). These dynamic features may be calculated from the acquired and processed temporal signals or images of the eyes of testee. According to some embodiments, no real-world coordinates of the eye's location are required. Eye-dynamics, similarly to eye-movements, are influenced by a variety of factors (mental effort, emotional state, a person's attributes & current-status, the stimulus, the environment), thus they can capture variations within and between people. For example, FIGS. 5A and 5B depict a trajectory of a moving target (52 of FIG. 5A and 53 of FIG. 5B) and the acquired corresponding eye-movements (51 of FIG. 5A and 54 of FIG. 5B) of 2 different people, as acquired by our system. The eye-path dynamics (51,54) is an example of an eye-dynamic signal including both responsive and non-responsive eye-dynamics. As can be seen, the eye trajectories (51,54) include a responsive element, which is the tracking of the eyes after the moving target. In addition, eye trajectories (51,54) include "noise"—it includes internal/intrinsic dynamic elements not correlated to the visual task (tracking the target) and may be referred to as non-responsive eye-dynamics. One can observe that the "intrinsic-noise" is different from person to another.

Advantageously and according to some embodiments, eye-dynamics may be easier to acquire than eye-movements. This is since the actual spatial position may not be calculated and required, rather, only the dynamic information may be needed, thus simpler hardware may be used, and no calibrations are required. Advantageously, since eye-dynamics are dynamic oriented signals, they have a better signal to noise ratio, and hold more information than other eye signals.

Protocols for the Deception Detection Eye-Session

The deception detection system and method use, in accordance with some embodiments, a specially designed deception-detection eye-session that includes algorithms and protocols, which have been developed for the task of detecting liars from their eye dynamics. The algorithms and protocols are responsible for acquiring enhancing and preserving eye-dynamics of a testee (the person being investigated, tested, checked or screened). These protocols were designed specially to enhance and preserve information in a testees eyes, which is indicative of whether he is "cheating" (lying, deceiving, concealing information, ignoring, being uncooperative, or manipulative), and to improve the performance of the "deception detection" system in terms of reliability, sensitivity and specificity. In some embodiments the protocols may include: a stimuli-sequence, a visual task, a relaxing element, additional protocols or any combination thereof.

Stimuli-Sequence Protocol

According to some embodiments, the system presents the tested subject predesigned stimuli-sequence and calculates his eye-dynamic. The eye-dynamic signals may include responsive and non-responsive components. The dye-dynamic signal is analyzed, and responsive components may be compared or processed together with baseline or non-responsive eye-dynamic signals.

According to some embodiments, the stimuli-sequence may include any of, or a combination of: evoking-stimuli, neutral-stimuli and intermediate-stimuli. The stimuli may include visual or auditory elements such as, but not limited to: questions, sentences, information, images, faces, places, photos, numbers, voices, noises, texts, but also other stimuli like smell, tactile elements, etc. The stimuli may be presented as one sequence/set or in a few sub-sets, and some of them may be repeated. Several stimuli sub-sets may be used in an investigation. Often the session includes presenting several stimuli-sub-sets. In some embodiments, at least some the stimuli, sub-sets, or the sequence are presented more than once. Stimuli may be of a general nature or may be designed for a specific investigation, task or person (personalized).

According to some embodiments, any stimuli-sequence should include at least one evoking-stimuli. The evoking-stimuli are used as a means for creating different responsive eye-dynamics from testees, which are correlated to their current status, for example: honest/lying, cooperative/uncooperative or deceitful/honest. Examples of different responsive eye-dynamics include, but are not limited to: atypically avoiding or atypically reacting or typically reacting or typically not reacting.

The evoking-stimuli may be any type of element that can potentially evoke a reaction from certain testees in certain circumstances, which differentiates between truthful-lying, cooperative-uncooperative, deceitful-honest, and which creates a response that is detectable in the testee's eye-dynamics signals.

The evoking-stimuli may be embedded with other types of stimuli, for example neutral-stimuli and/or intermediate-stimuli. A neutral stimuli is designed in a way that it usually does not evoke a response from testees, or it evokes a response from most testees, or alternatively some testees react to it, but these testees' reaction will be different than their typical reaction to an evoking-stimuli, when he is lying. Thus, the testees' response to a neutral-stimuli are not correlated to their current status: honest, lying cooperative, uncooperative or deceitful.

For example, the system, according to some embodiments, may be used to detect a terrorist planning to board a plane with explosives in his suitcase at the airport. In this case, the evoking-stimuli could be an image of explosives (with or without a corresponding vocal question), and the neutral-stimuli may be any other standard images (bird, car, flower). In this stimuli-sequence the terrorist's eye-dynamics will react atypically to the image of the explosives, while innocent testees will react typically to all images of evoking-stimuli and neutral-stimuli. In another example from the same scene, the stimuli could be questions. The evoking-stimuli could be a question such as: "Do you have explosives in your bag? and then natural-stimuli could be questions such as Is this your suitcase? Is your name Mr. Smith? etc. The testee may be asked to answer the questions, but this is not necessarily required.

In some embodiments, intermediate-stimuli may be embedded in the stimuli-sequence. The intermediate-stimuli characteristics vary depending on their goal. For example, they can be designed to make a testee's eye-dynamics signal remain or return to its unexcited "baseline" between stimuli (evoked and neutral). This improves signal to noise ratio of the eye-dynamic signals, thus improving the system's capability to detect liars. An example of such an intermediate-stimuli is a uniform screen or a uniform screen with one simple element embedded in it. The embedded element may be standing-still, flickering or moving.

The testee's response to any stimuli may be affected by many factors, among them, but not limited to them, are: content, duration, intensity, location, pitch, familiarity and color. His response is also affected by factors such as the duration between consecutive stimuli and by the ambient conditions of the environment, where the investigation takes place (noisy, friendly, dark/bright). Accordingly, all these factors should be considered when designing the stimuli-sequences.

During the deception-detection eye-session, the protocol may require the testee to reply, remain idle or both, to a stimuli. His reply may be auditory, physical or in any other noticeable manner. For example, for a stimuli-sequence, which includes questions, the testee may be required to answer some questions (stimuli) out loud, and for others he may be required to stay silent. In another example of the embodiment, for yes/no questions, the testee may be required to select the answer (yes or no) with a nod of the head, a hand gesture, a wave of the hand, using a mouse or a touch screen for some questions and to stay idle for others.

The stimuli-sequence design may be based on any of the different protocols and methods used in standard polygraph investigations and in any other type of practiced investigation. It may also be based on new investigation protocols and schemes. For example, the stimuli may be a set of auditory questions, visual questions, images or sounds with the relevant-irrelevant testing technique, designed to gauge reactions of subjects against "crime" questions and other "non-crime" related questions. Sometimes "diagnostic" questions are used. The different types of questions alternate. In another example, the stimuli may be a set of auditory questions, visual questions, images or sounds, using the Guilty Knowledge Test (GKT), or the Concealed Information, Test (CIT), testing the participant on his knowledge of the crime that would not be known to an innocent person.

According to some embodiments, when designing a stimuli-sequence protocol, the duration between the stimuli elements is optimized to obtain high throughput and reliable results. According to some embodiments, the stimuli-sequence protocols consider the length of the different stimuli and the different duration of their corresponding dynamic response, when designing the duration between the different elements.

In addition, according to some embodiments, stimuli-sequence protocols need to establish the chronological order of presenting the different stimuli, the division of the stimuli to subsets (if required), and the number of repetitions of each stimuli. These factors influence the throughput and performance of the system.

In some embodiments, it may be required to hide that an investigation is being performed or to hide the nature and technology of the investigation. In these embodiments, the stimuli may be designed to be unnoticeable to testee, i.e. camouflaged in another task.

The stimulus-sequence may be prerecorded or presented to testee in a live session by a presenter (operator, investigator, technician). In a prerecorded session, the different stimuli may be presented at fixed and known time slots. In a live session, the presenter may present the stimuli at fixed and known time slots, or alternatively, present the stimuli based on the progress of the investigation and his subjective judgment.

In some embodiments, which are based on a live session, the presenter may decide when is the optimal time to present each stimulus, based on real time physiological information from testee. For example, by monitoring physiological signals that are triggered and controlled by the sympathetic or para-sympathetic nervous system, the operator may select an optimal time slot for presenting each stimulus. Thus, for example, by monitoring a testee's physiological indicators of stress such as sweat, which may be measured by galvanic skin response (GSR), heart rate or respiratory rate, the operator may present each stimulus in correlation with the testee's stress level. Some stimuli responses may be more easily detected when the testee is relaxed and some may be more easily detected when the testee is stressed. Thus, in accordance with some embodiments, stimulus triggering, based on physiological indicators, may improve the system's signal-to noise-ratio, thus enhancing the system's capability for detecting liars.

Figure 7:
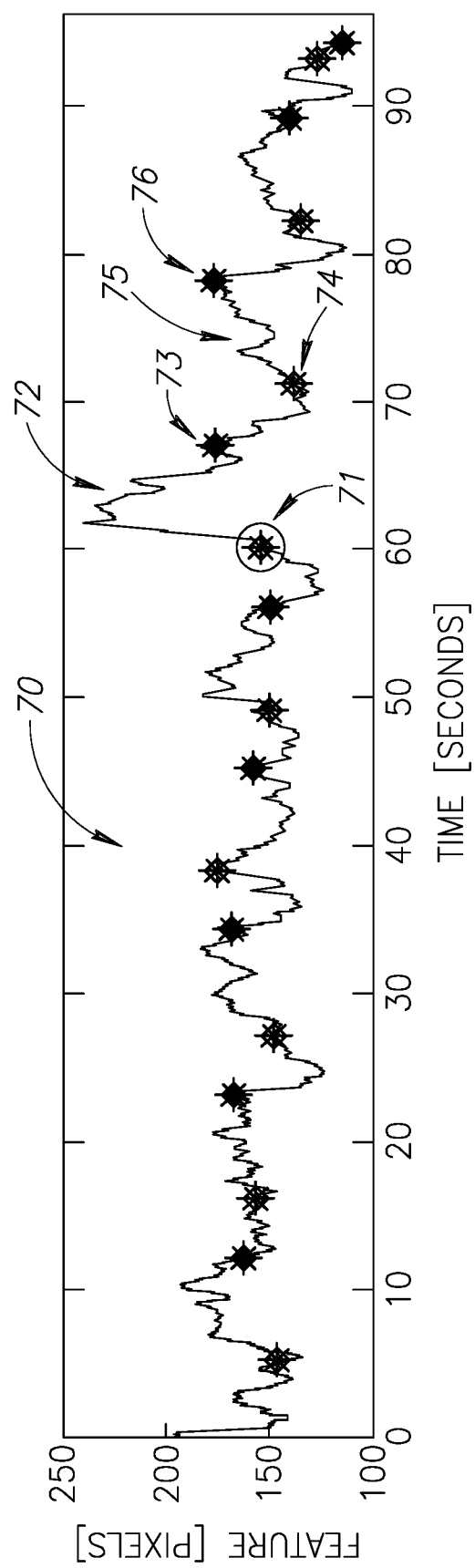
FIG. 7 depicts an example of an eye-dynamic signal based on pupil dynamics, in response to a stimuli-sequence, according to some embodiments.

Reference is now made to FIG. 7, which depicts an example of an eye-dynamic signal 70, acquired in response to a stimuli sequence. Signal 70 is based on pupil dynamics. As seen, eye-dynamic signal 70 includes responsive elements, the pupil dilates significantly in response to a stimulus, and non-responsive dynamic elements (intrinsic noise) uncorrelated to the exposure to any stimulus.

Mark 71 represents the time when the testee was presented with an evoking stimulus, Mark 73 represents the time when the testee was presented with an intermediate stimulus, Mark 74 represents the time when the testee was presented with a neutral stimulus, and Mark 76 represents the time when the testee was presented with another intermediate stimulus.

It can be seen that after testee's exposure to evoking-stimulus (Mark 71) and neutral-stimulus (Mark 74), there is a correlated response of pupil dilation (72 and 75 respectively). The signal reaches a peak and starts decreasing back toward its value prior to the stimuli. In contrast, Marks 73 and 76, which represents the time when the testee was exposed to an intermediate stimulus, do not evoke any correlated eye-response. In addition, it can be seen that the responsive component of signal 75 is milder than the responsive component of signal 72, thus demonstrating an example of how a response to an evoking-stimulus may differ from a response to a neutral-stimulus.

Visual-Task Protocol

In accordance with some embodiments, during the deception-detection eye-session, as part of the protocols disclosed herein, the testee will be asked to perform at least one visual task. During the visual task, the testee watches any type of visual element that results in an eye-response from testee on the one hand (examples: smooth-pursuit motion of the eyes, as a response to a moving target, fixation, saccades, scanning of the eyes, as a response to a display of a still object or objects), and in some type of influence on the testee, on the other hand. The influence on testee may be, for example, an influence on his mental effort or emotional status. Such influence on testee may evoke physiological and/or psychological responses, such as, but not limited to: cognitive load, stress, relaxation, interest, familiarity, sweat, change in heart rate, change in blood pressure, etc.

According to some embodiments, the visual task protocol will typically be performed simultaneously with the stimuli-sequence protocol. In some embodiments, the visual task may be designed as an independent task, in other embodiments it may be designed as an integral part of the stimuli-sequence, i.e. a single task serves as the visual task and the stimuli-sequence. In some embodiments, which use a sequence of images as the visual task, the same images may be used as part of the evoking-stimuli. In other embodiments, the visual task is independent of the evoking-stimuli, which may be, for example, an auditory evoking-stimuli.

In some embodiments, the visual task is customized. For example, it is designed to best work with specific stimuli-sequences, or with a specific testees (personalization) or for a specific investigation.

According to some embodiments, the visual task should be designed in a manner that the task itself will not evoke undesired and unexpected eye-response and eye-dynamics from the testee. Accordingly, factors such as: intensity, size, location, illumination, color, shape, content, familiarity, duration, velocity, amplitude of the visual task and the testee's ambient environment, should be considered carefully, when designing the visual task.

The visual task may be displayed on or with any type of platform. Examples include, but are not limited to, a monitor, a mobile device, a set of LEDs, real 3D objects (metronome, objects related to investigation), holograms, people, goggles, glasses etc.

The visual task may have more than one goal, thus it is pre-designed and used in the deception-detection eye-session protocol according to its designated goals. The visual task goals include, but are not limited to: making it difficult for testee to cheat, being part of the counter-measure tools, improving eye-dynamic base-line, helping hide the existence of an investigation or its nature and enabling synchronization.

In some embodiments, the visual task may be designed and used to synchronize the stimuli-sequence and testee's responses, as detailed herein.

In some embodiments, the visual task may be designed to improve the system's signal-to-noise-ratio. The visual task is pre-designed and known, thus a testee's typical response to it is known and expected, thus a testee's response to the visual task may be controlled to some extent. Accordingly, in some embodiments, the visual task is designed to provide better control on the base-line eye-dynamics signals of testee. The baseline signals are those, which are not part of a testee's response to the stimuli-sequence. This type of design improves the system's signal-to-noise ratio resulting in improved deception detection capabilities.

In some embodiments, it may be required to hide that an investigation is being performed or the nature and technology of the investigation. In these embodiments, the visual tasks are designed to be unnoticeable, e.g. camouflaged in other tasks.

Without being bound to any scientific theory, deception (lying, cheating, ignoring, being uncooperative, manipulating) creates cognitive load on the cheating party. Thus, to deal with a cheater, one may either make it difficult for him to engage in activities, which require additional cognitive load such as cheating, or alternatively detect additional cognitive load, when it occurs.

Accordingly, in some embodiments, the visual task is designed to make it difficult for the testee to cheat. More specifically, the visual task is designed to create just the "right" amount of extra cognitive load to make it difficult for the testee to cheat. The "right amount" means that the visual task protocol, together with the stimuli-sequence protocol, create a cognitive load that makes it difficult for the testee to concentrate on any additional cognitive task, such as cheating. The more challenging, complex and fast the visual-task is, the more cognitive load it creates. To test if the visual task does not create too much cognitive load, one should evaluate the performance of the testee to the visual task during a stimuli sequence. If the testee's performance of the visual task is not good, this means that the task is too challenging. The "right visual-task" may vary from person to person.

However, if the testee tries to cheat, the system can usually detect this attempt. In some embodiments, counter-measure algorithms may be applied (see for example, FIG. 3, 316) to evaluate the testee's performance of the visual task, and use the results to help decide, if the testee is cheating. If the algorithms detect bad performance of the Visual-Task or an attempt by the testee to ignore the visual task (to reduce cognitive load), they will raise a "Red-Flag" indicating a high probability of the testee cheating. Thus, the visual task together with the eye-dynamic signals and the counter-measure algorithms enhance the system's deception detection capability by providing a high-performance counter-measure capability to the system.

An example of a visual task is a moving target/object, which the testee is asked to follow/track with his eyes. The target/object may move at different velocities, ways, patterns and trajectories. It may move for example in: a pre-defined complex pattern, a simple repeatable pattern, a random pattern, or any combination of these. It may, for example, move smoothly or in jumps, fast, slow, or with changing velocities. It may, for example, move in linear patterns, in a closed shape trajectory like a circular motion, or in a curved motion pattern. The target/object may, for example, stand still in a specific location or move slightly in its fixed location or flicker in its fixed location. The visual task may include one of these patterns and characteristics or be a combination of any of these visual task elements. FIGS. 5A 52 and 5B 53 are examples of a visual task which includes a continuous moving target in a predefined trajectory. In some embodiments, the visual task is a single target moving from side to side repeatedly. In this example, if the testee tries to cheat in connection with the stimuli-sequence, this will increase his cognitive load and thus may compromise his tracking performance. The counter-measure algorithms will check the testee's tracking performance by any standard method used to compare two signals (target trajectory and eye trajectory) in qualitative or quantitive manners (correlation, standard deviation, error, MLS, smoothness, etc). If the algorithms detect bad tracking performance or no tracking of the target/object task by testee, they will raise a "Red-Flag" indicating a high probability of the testee cheating.

An example of bad tracking performance is disclosed in FIG. 5A hereinabove. In this example, eye trajectory 51 is extremely noisy and exhibits bad tracking, indicating high cognitive load, which may indicate an attempt to cheat. In this case the algorithm will raise a "Red-Flag" indicating a high probability of the testee cheating. This process is disclosed in FIG. 3, in accordance with some embodiments.

In another example, the visual task is composed of a sequence (at least one) of still images/objects. The testee is asked to naturally scan the images, and sometimes he may even be asked to perform an assignment. Since people scan certain images/objects in a characteristically typical way, atypical or irregular scanning of the images/objects by the testee may imply that the testee is uncooperative or uncomfortable with the images/objects or is cheating. Atypical scanning may be defined by comparing someone's scanning to his own scanning patterns of other images/objects or alternatively defined as comparing someone's scanning to the pattern of other people. The atypical or irregular scanning patterns are detected by the counter-measure algorithms, based on the visual task and the eye-dynamics signals. If the algorithms detect atypical or irregular scanning patterns, they will raise a "Red-Flag" indicating and an uncooperative testee with a high probability of being a cheater.

Relaxing-Element

Any investigation or screening process is a stressful event for cheaters, but also for cooperative and non-cheating truth telling testees. In some situations, to enhance the performance of the deception-detection eye-session, it is best to get the testee as relaxed, calm and emotionally unstressed as possible. This may help keep the testee's eye movements and eye-dynamics patterns as natural and neutral as possible during the test, maintaining a better baseline signal, thus providing a better signal to noise ratio. This results in an improved capability of the system to detect liars.

In some embodiments, the deception-detection eye-session protocols include a relaxing element. This element may be any type of element that the testee is exposed to and makes him more relaxed. The relaxing element may be part of the visual task or part of the stimuli-sequence or an independent element. It may also be customized to a certain situation, investigation or testee (personalization). In one embodiment, the relaxing element is a moving target moving periodically from side to side, which the testee is asked to track with his eyes. Another example of adding a relaxing element to the protocol is by designing and using the neutral stimuli and intermediate stimuli as relaxing elements.

Additional Protocols

In some embodiments, additional protocols may be used to collect and deploy additional data, reference data, to improve the detection of liars and cheaters during a deception-detection eye-session. In some embodiments, the reference data is used as input in the fusion stage; in some embodiments it is used to better design the different protocols; in other embodiments, it is used in conjunction with the counter-measure algorithms. Yet, in some embodiments, the reference data is used in more than one of the stages: fusion, protocols and countermeasure algorithms.

In some embodiments, the reference data may be collected from the testee just before or after or before and after the deception-detection eye session/investigation. In this embodiment, a personalized reference data is created and used. In other embodiments, the reference data may be collected a-priori from a typical population, and may be used to create a generic reference data, to be used in a deception-detection eye-session/investigation.

In some embodiments, the reference data is collected using a specially designed preliminary sequence of stimuli: reference stimuli sequence. In some embodiments, the reference stimuli sequence includes any of, or a combination of: evoking stimuli, neutral stimuli and intermediate stimuli. The stimuli may include visual or auditory elements such as questions, images, faces, photos, numbers, voices, noises, texts, but also other stimuli like smell, tactile elements, etc. The stimuli may be presented as one sequence or in a few sub-sets. Several stimuli sets may be used. Often the session includes presenting several stimuli sets and presenting at least some of them (stimuli or stimuli set) more than once. All stimuli may be of a general nature or may be designed for a specific investigation, task or person (personalized).

In some embodiments, the reference data is collected using a reference stimuli sequence. In some embodiments, this is done for the testee, just before/after he is exposed to the stimuli sequence protocol, thus creating a personal reference data for the testee. In some embodiments, the reference data is collected from people who are not suspects at this moment (with no connection to any investigation at this moment). This is like an enrollment session. The collected data creates a personal reference-data for each specific person, which may be used, if needed, in the future, during a person's deception-detection eye-session/investigation. In other embodiments, the reference data is data collected from a typical population, while they respond to a reference stimuli-sequence. The collected data is used to create a generic reference data, to be used in a deception-detection eye-session/investigation.

In some embodiments, the testee goes through a simulation session (training session) to familiarize him with the different protocols of the eye session. This improves the testee's performance during the real deception-detection eye-session/investigation, thus improving the system's detectability capabilities.

Counter-Measure Algorithms

People have found ways to try and cheat known lie detection systems. Some people have been known to take sedatives to reduce anxiety; using antiperspirant to prevent sweating; and positioning pins or biting parts of the mouth after each question to demonstrate a constant physiological response.

The deception detection technology, in accordance with some embodiments, may include unique counter measure algorithms (see for example, FIG. 3, 316) that are effective in detecting cheaters, i.e. people who are trying to influence the results of the system (manipulate the system), are uncooperative, deceiving, or ignoring the protocol. The counter measure algorithms, in accordance with some embodiments, use inputs from the Eye-Dynamic signals to detect these testees. In some embodiments, the counter measure algorithms use, in addition, inputs from the visual task, the stimuli sequence, the extracted parameters, or any combination of these inputs.

According to some embodiments, the counter measure algorithms, based on their inputs, calculate at least one deception indicator. The probability of the testee being deceptive (algorithm's output) depends on the algorithm's analysis of the deception indicators. In some embodiments, the output (conclusion) of the counter measure algorithms is used as input to the fusion stage, in some embodiments it is used as feedback to the system's operator, and in some embodiments, it is used as input for both. The operator may use the output of the counter measure algorithms to interact with the testee, or to make any required changes in the eye session.

In some embodiments, as detailed herein, particularly in the visual task section, the visual task may be used in conjunction with the counter-measure algorithms to detect cheaters. For example, if the counter measure algorithms detect any of or all of the following: bad tracking performance of the visual task, an attempt by the testee to ignore the visual task, atypical scanning patterns or/and irregular scanning patterns, they will update a corresponding deception indicator that will be analyzed by the algorithms and used to calculate the probability of the testee being a cheater.

Eye-Dynamic signals reflect many attributes of the testee. According to some embodiments, the variety of parameters calculated from the Eye-Dynamic signals capture this information on the testee. According to some embodiments, the system's "holistic" approach, which sees the whole picture on the one hand, and knows to identify its details, on the other, is an important asset, used by the counter measure algorithms to detect deception of any kind. Thus, the dynamic of parameters, may be used as deception indicators. For example, in some embodiments, parameters indicating stress with irregular dynamics, may be a sign of a testee attempting to cheat the system. This information is used by the counter measure algorithms as part of its decision if a testee is deceitful. In another example, in some embodiments, parameters indicating cognitive load with irregular dynamics or values, may be a sign of a testee attempting to cheat the system. This information is used by the counter measure algorithms as part of its decision if a testee is deceitful.

Synchronization

According to some embodiments, during the deception detection eye session, the system collects both responsive and non-responsive eye dynamic signals from the testee. The system needs to detect if and when a testee is atypically avoiding or atypically reacting or typically reacting or typically not reacting to a specific stimulus. Thus, according to some embodiments, a timing mechanism is applied. This timing mechanism is configured for a correlation and/or synchronization scheme between the stimuli sequence and the testee's eye dynamic signals. The system is configured to know when a new stimulus is presented to the testee, when it ends, which stimulus is presented, and what was the corresponding response of the testee to the stimulus. The system is configured to create a time stamp, which synchronizes the acquired eye dynamics and the stimuli sequence. The synchronization is required for standalone embodiments as well as for add-on configurations of the system (for example, the use of an external display unit such as mobile device, goggles, virtual/augmented reality device, etc.).

In some embodiments, dedicated hardware and/or software are used for synchronizing the testee's eye dynamic with the stimuli sequence and sometimes with the visual task. For example, a controller may manage both stimuli sequence exposure to the testee, visual task and eye dynamic acquisition, thus making sure they are in synch. There are many additional embodiments to deploy such timing mechanism for the system.

In some embodiments, the visual task is used for synchronization. In these embodiments, the stimuli sequence is exposed to the testee in synch with the visual task (a stimulus is presented each time the visual task begins or at a specific point during the visual task). Since the visual task has a recognizable pattern in the eye dynamic response signal, and the stimuli sequence is in synch with it, we obtain indirect synch between the stimuli sequence and the eye dynamic signal.

In another embodiment, the stimuli sequences are prerecorded, thus their time stamp is known; accordingly, the system is synchronized.

Yet in another embodiment, physiological synchronization is used. In this embodiment, the system or the system's operator monitors and analyzes the testee's eye dynamic signal in real time, and present each element of the stimuli sequence to the testee at an "optimal time". In other words, according to theses embodiments, it is best to present the testee with a stimuli sequence element, at a time when his response is the most noticeable—optimal signal to noise ratio. This type of synchronization enhances the system's capability of identifying irregular eye dynamic patterns correlated to cheating, thus improving the system's deception detection performance. For example, the pupil dilates and contracts regularly and continuously for various reasons. Thus, an optimal pupil response to a stimuli sequence element will be obtained, when the testee's pupil is contracted before the testee is exposed to the stimulus. At this moment the testee's response will be the easiest to detect. Accordingly, by monitoring the pupil size from the testee's eye dynamic signal and presenting the stimuli sequence elements when the pupil is contracted, we obtain synchronization and a better detection of eye dynamic cheating responses. In another embodiment, based on physiological synchronization, the system or system's operator/presenter will monitor eye dynamics in a non-responsive setting (calm situation, no stimuli, minimal cognitive load). This will enable identifying the correct moment to expose a stimuli sequence element.

In another embodiment, the stimuli sequence is pre-recorded by video, and includes synchronization information in it. For example, one of the audio channels of the stimuli's sequence video may be used to encode this information for each frame. This can be done in any available audio format such as, but not limited to: AM modulation, FM modulation, pulse wide modulation (PWM), etc. The encoded synchronization information may be transferred to the eye dynamic signal recording by any available method such as, but limited to: audio cable, free sound, WiFi, Bluetooth, etc. In addition, the audio information may be translated to other formats, which may be embedded in the eye dynamic signal recording. For example, the audio synchronization information may be translated to a light source (LED, for example), which can be detected by the camera and seen in the response video.

In yet another embodiment, the stimuli sequence or visual task embeds the synchronization information in the images of the video. This may be done, for example, in text, barcode, flickering intensity, etc. Another option is to encode the information using a light source (LED, for example), which can be detected by the camera and seen in the response video.

Acquisition

The acquisition device(s), system(s) and method(s) (e.g., hardware software and algorithms) is responsible, according to some embodiments, for acquiring temporal signals and/or images of the testee's eyes, during his participation in the different protocols of the deception detection eye session. The acquired signals and images include both responsive and non-responsive dynamics of the eyes.

Responsive dynamic data of the eyes may be defined, in accordance with some embodiments, as any eye-dynamic data, which is evoked or influenced by one or more elements/parts/features of the eye session protocols.

Non-Responsive dynamic data of the eyes may be defined, in accordance with some embodiments, as any eye-dynamics data, which is not correlated, influenced or connected to the eye session protocols. Non-responsive dynamic data of the eyes exists, since a person's eyes continuously move, blink, and his pupils continuously dilate and contract, even when he is not externally evoked.

An example of responsive dynamic data is eye-tracking movement, while following a moving target, and an example of non-responsive dynamic data is involuntary and automatic eye movements. Examples of these two types of eye dynamics can be seen together in FIGS. 5A and 5B. Trajectories 52 and 53 disclose the trajectory of the moving target and trajectories 51 and 54 disclose the trajectory of the eye, which includes both responsive and non-responsive components. As can be seen in FIGS. 5A and 5B, the eye trajectory includes non-responsive elements, which may be referred to in this example, as "noise", which includes internal/intrinsic dynamic elements not part of the visual task (tracking the target). In addition, one can observe the tracking trajectory of the eye.

According to some embodiments, the acquisition stage includes a processing stage, which is focused on enhancing and preserving the eyes dynamics and characteristics (see for example, FIG. 3, 310), and calculating the eye-dynamic signals from signal and image (see for example, FIG. 3, 312), using a processing unit. The processing stage may include, any of, or any combination of, but is not limited to: pattern recognition (detection of face, eye, iris, pupil, nose, eyebrows), blink detection, blink removal, interpolation, extrapolation, filtering, scaling, histogram stretching and manipulation, thresholding, binarization, connected-component analysis, sensor movement/noise detection and removal, synchronization, head movement detection and correction, etc. The processing stage may depend, among other things, on the type and quality of the sensor, the testee and the environmental conditions. According to some embodiments, care should be taken during the processing stage not to filter out or throw out dynamic information and other eye characteristics.

According to some embodiments, since the deception detection technology (system and method) is based on the analysis of dynamic characteristics, behaviors, changes and variations of the eyes, ("Eye-Dynamic"), the acquisition system and method are focused on preserving and enhancing the dynamics and characteristics of the different eye signals, and not on acquiring and delivering the eye's real position. Thus, deception detection acquisition is designed to provide high-resolution and an improved dynamic response signal at the expense of obtaining the eye's exact location. According to some embodiments, since the eye's position in the real world is not necessarily of interest in the current system, calibration of the system is not required, like in most other eye-based technologies.

The acquisition may be done with any suitable means available in the market such as, but limited to: EOG (Electro-oculography), MOG (Magneto-oculography), or VOG (Video-oculography-Video eye trackers). The VOG sensor, is based on pupil detection from the images, and may include any type of camera, including but not limited to, a black and white camera, a color camera, an infra-red sensitive camera, a near infra-red sensitive camera, a three-dimensional camera, or any combination thereof. However, other types of cameras may be used. The sensor may include an analog video, a CCD, a CMOS, an Ober detection apparatus, a photodiode set-up, or a combination thereof. In some embodiments, a single sensor is used, in other embodiments more than one sensor is used. In some embodiments, the signals or images are acquired from both eyes, in other embodiments they are acquired only from one eye, and in some the acquisition may be alternately from both eyes.

The system can work with available, ambient light. However, in some embodiments, means for illumination are added. The additional illumination, in some situations and conditions, makes sure the face and eye area are lit properly, improving the quality of the acquired signals and images, thus resulting in improved performance by the system. The illumination may be in any frequency including the visual spectrum and the near IR spectrum. Filters may be added to the sensor to improve its performance. In some embodiments, which include additional illumination, at least one near IR LED is used for illumination. In these embodiments, a filter may be added to the sensor to block all components of the ambient light and leave only the near IR light spectrum.

In one embodiment, two CMOS cameras in conjunction with image and signal processing are used to acquire and calculate eye dynamics. The cameras use high frame-rate (60-240 frames/second) to better capture the dynamic characteristics of the signals. The eye dynamic signals include: pupil dynamics, blink dynamics, head dynamics (head movements cause, indirectly, eye movement), eye movements dynamics in X direction, eye movements dynamics in Y direction.

It is noted that, in accordance with some embodiments, the acquisition procedure (using any acquisition device(s) and system(s)) may be conducted at a remote location, such as an interrogation room or an airport, distant from the place where the data processing is conducted.

Processing & Fusion

In accordance with some embodiments, information, parameters and/or data may be extracted from the eye dynamic signals. The extracted information/parameters/data (see for example, FIG. 3, 314) may reflect different attributes of the testee and his current status such as any of, or any combination of, but not limited to: emotional state, state of mind, injury, illness, mental effort, current-status, cognitive status, neuropsychological status, neurophysiological status, intoxication (alcohol, drugs) and individual characteristics. The extracted parameters may also reflect the influence of the different stimuli, the visual task, and the environment on the testee. The extracted information/parameters/data may include both responsive non-responsive information.

Examples of extracted information/parameters/data may include, any of, or any combination of, but not limited to: trajectories, direction information, velocity, vectors, frequencies, saccades, Convergence, Rolling Pursuit, Nystagmus, Drift, Micro saccades, Physiological Nystagmus, tracking quality, tracking performance, scan-paths, timing information (for example: delay in response, fixation duration, relaxation and rising coefficients), shape-morphological information (signal smoothness, signal to noise ratios, symmetry, shape), integral values, peak values, rising and falling characteristics, etc.

Since, the extracted information/parameters/data exist simultaneously in the eye-dynamics signals, and since they reflect and are influenced by a variety of factors, and since some of these may be more relevant than others, a holistic approach may be used to determine if a testee is lying. The holistic approach may be deployed in the analysis stage by fusion algorithms (see for example, FIG. 3, 318). In accordance with some embodiments, this stage is responsible for detecting liars by identifying, understanding and considering the whole picture on the one hand, and the fine details, on the other hand. The fusion algorithm transforms all this data into meaningful information, which delivers the probability of the testee lying (see for example, FIG. 3, 320). The fusion algorithms may include, for example: neural-networks, Deep-Learning, Fuzzy-Logic, classifiers, decision Tress, etc. One of the advantages of the deception detection systems and methods is that they may be automatic and autonomic and does not require an expert investigator.

In accordance with some embodiments, the fusion algorithms use as input the eye dynamic signals. In some embodiments, the fusion algorithms may use any of or any combination of the following: eye dynamic signals, extracted parameters, the output of the counter-measure algorithms, the evoking stimuli protocols and the visual task protocols (see for example FIG. 3). In some embodiments, additional inputs may be used (separately or in any combination) by the fusion algorithms, such as, but not limited to: reference data, environmental conditions, previous collected data, synchronization information, relaxing element, personal information about the testee and information about the investigated event.

In some embodiment, only information/parameters/data indicating mental effort (for example: cognitive load, non-cooperative behavior) and emotional state (for example: surprise, familiarity, stress) may be extracted from the eye dynamics signals and used as input to the fusion algorithm. This approach is based on the scientifically proven findings that the eyes respond to both stress and cognitive load, which are both strong indicators of lying.

In some embodiments, the deception-detection eye session includes at least 2 repetitions of the stimuli sequence and the visual task protocols. From each session eye dynamic signals are calculated, and from each eye-dynamic signal information/parameters/data may be extracted. The information/parameters/data are synchronized (as described before) with the protocol events (for example, presentation of evoking stimuli, presentation of other stimuli, visual task performance). The fusion algorithms analyze and compare this data to calculate the probability of the testee being deceptive.

Figure 6:
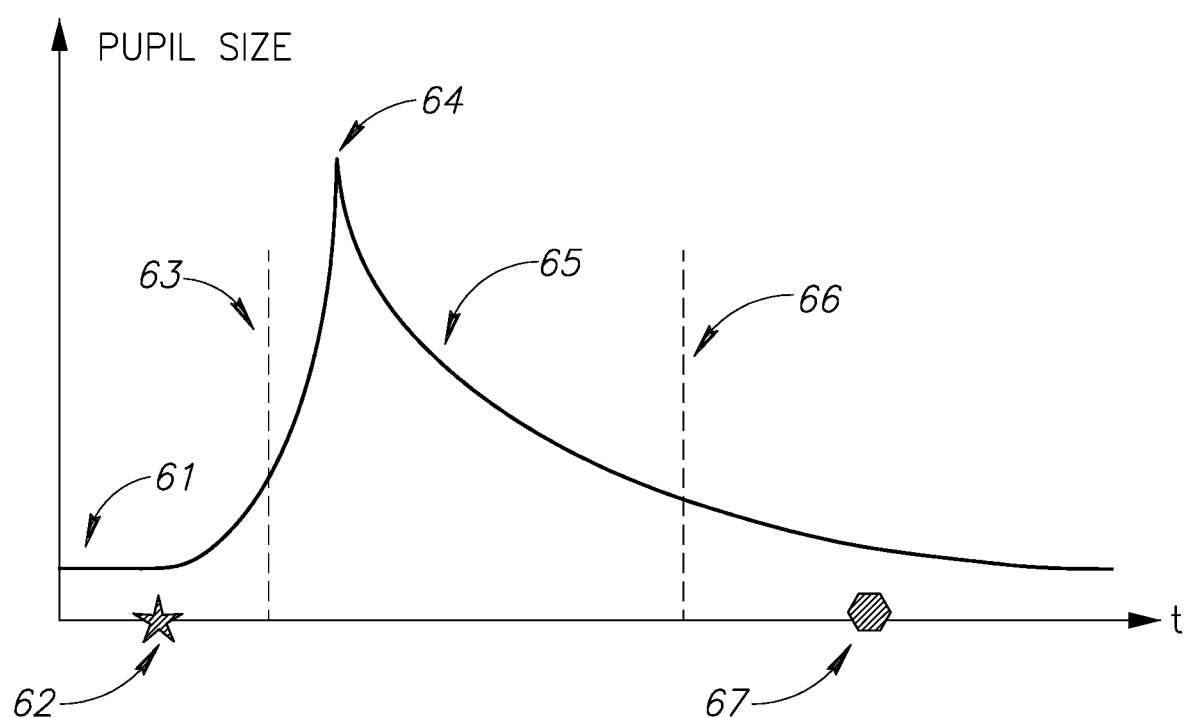
FIG. 6 depicts a graph of pupil temporal dynamics in response to an evoking stimulus, according to some embodiments.

In some embodiments, for each stimulus in a stimuli-sequence, several parameters are calculated from the corresponding dynamics signals. Reference is now made to FIG. 6, which depicts a responsive eye-dynamic signal to a stimulus (pupil temporal dynamics in response to an evoking stimulus). Mark 62 represents the time where a stimulus is presented to the testee. As can be seen, a typical reaction to a stimulus may be a rapid pupil dilation from base line value 61 to peak value 64 and a slower decline 65 back to base line values. An example of a parameter extracted from such a signal is the value of the peak amplitude of signal 64. Another example of an extracted parameter is an integral of the response signal. The integral can be calculated from the time of providing evoking stimulus Mark 62 to the testee to the time of providing the next stimulus Mark 67. In another example, the integral is calculated only during the central part of the response signal, between Mark 63 and Mark 66.

The different parameters may be used by the fusion algorithm to identify when a testee is lying. In some embodiments, the integral values of each responsive eye dynamic signal to a specific stimulus are calculated and compared. The fusion algorithms may compare these values, and decide that the testee is lying if, for the evoking stimuli, the integral value is the highest in the sequence. In other embodiments, the peak values of each responsive eye dynamic signal to a specific stimulus are calculated and compared. The fusion algorithms may compare these values, and decide that the testee is lying, if for the evoking stimuli the value is the highest in the sequence.

An example of a pupil dynamic signal during a stimuli sequence is disclosed in FIG. 7. In this example, after providing an evoking stimulus (Mark 71), the calculated peak and integral of the responsive signal 72 are the highest compared to all other responsive signals such as signal 75, thus indicating a high probability of the testee being deceptive. Thus, the fusion algorithm will suspect that the testee as cheating. If this event reoccurs in another sequence, then the probability of the testee cheating increases. If at the same time the testee's visual task score is low (indicating increased cognitive load), then this further increases the probability of him being a liar. Voting techniques may be used by the fusion algorithms to combine the results.

In the description and claims of the application, the words "include" and "have", and forms thereof, are not limited to members in a list with which the words may be associated.

As used herein, the term "about" may be used to specify a value of a quantity or parameter (e.g. the length of an element) to within a continuous range of values in the neighborhood of (and including) a given (stated) value. According to some embodiments, "about" may specify the value of a parameter to be between 80% and 120% of the given value. For example, the statement "the length of the element is equal to about 1 m" is equivalent to the statement "the length of the element is between 0.8 m and 1.2 m". According to some embodiments, "about" may specify the value of a parameter to be between 90% and 110% of the given value. According to some embodiments, "about" may specify the value of a parameter to be between 95% and 105% of the given value.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable sub-combination or as suitable in any other described embodiment of the disclosure. No feature described in the context of an embodiment is to be considered an essential feature of that embodiment, unless explicitly specified as such.

Although steps of methods according to some embodiments may be described in a specific sequence, methods of the disclosure may include some or all of the described steps carried out in a different order. A method of the disclosure may include a few of the steps described or all of the steps described. No particular step in a disclosed method is to be considered an essential step of that method, unless explicitly specified as such.

Although the disclosure is described in conjunction with specific embodiments thereof, it is evident that numerous alternatives, modifications and variations that are apparent to those skilled in the art may exist. Accordingly, the disclosure embraces all such alternatives, modifications and variations that fall within the scope of the appended claims. It is to be understood that the disclosure is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the disclosure. Section headings are used herein to ease understanding of the specification and should not be construed as necessarily limiting.

What is claimed is:

1. A method for identifying if a subject is being deceptive, the method comprising:
    exposing the subject to a stimuli sequence, wherein the stimuli sequence includes a plurality of stimuli that includes at least one evoking stimulus and at least one neutral stimulus, and wherein the plurality of stimuli are presented sequentially in time;
    presenting a visual task to the subject, wherein the visual task requires the subject to track the position of a moving target;
    determining at least one of (i) bad tracking of the target by the subject and (ii) no tracking of the target by the subject during a plurality of time intervals, wherein each of the plurality of time intervals corresponds to a respective one of the plurality of stimuli;
    receiving, from one or more sensors, data indicative of pupil size of at least one eye of the subject, wherein the data includes a plurality of segments, and wherein each of the plurality of segments corresponds to a respective one of the plurality of stimuli;
    deriving, based on the pupil size data, at least one parameter that corresponds to each of the plurality of segments;
    determining a probability that the subject is being deceptive in response to a given one of the plurality of stimuli based on a combination of (a) whether bad tracking or no tracking was determined for the time interval that corresponds to the given stimulus and (b) the at least one parameter derived from the segment of data that corresponds to the given stimulus; and
    producing an output signal indicative of the determined probability.

2. The method of claim 1, further comprising applying one or more counter measure algorithms using the at least one eye dynamic signal to detect deception.

3. The method of claim 1, wherein the subject is further exposed to a relaxing element.

4. The method of claim 1, wherein an optimal timing for exposing the subject to a stimulus from the stimuli sequence is determined based on physiological activity and/or behavior indicators of the subject.

5. The method of claim 4, wherein the physiological activity of the subject comprises: eye dynamics, GSR, heart rate, respiration, body temperature, blood pressure, or any combination thereof.

6. The method of claim 1, wherein the at least one evoking stimulus comprises displaying an image to the subject.

7. The method of claim 1, wherein the at least one evoking stimulus comprises asking the subject a question.

8. The method of claim 1, wherein the at least one evoking stimulus comprises displaying an image to the subject and asking the subject a corresponding question.

9. The method of claim 1, wherein the at least one parameter that corresponds to each of the plurality of segments comprises an integral of the pupil size data for the respective segment.

10. The method of claim 1, wherein the at least one parameter that corresponds to each of the plurality of segments comprises (a) an integral of the pupil size data for each of the plurality of segments and (b) a peak of the pupil size data for each of the plurality of segments.

11. A system for identifying if a subject is being deceptive, the system comprising:
    a processor,
    a display configured to respond to instructions received from the processor; and
    one or more sensors configured to (i) detect the pupil size of at least one eye of the subject, (ii) track movement of at least one eye of the subject, and (iii) output data indicative of the detected pupil size and the tracked movement;
    wherein the processor is configured to
    (a) control the exposing of the subject to a stimuli sequence, wherein the stimuli sequence includes a plurality of stimuli that includes at least one evoking stimulus and at least one neutral stimulus, and wherein the plurality of stimuli are presented sequentially in time,
    (b) instruct the display to present a visual task to the subject, wherein the visual task requires the subject to track the position of a moving target,
    (c) determine, based on the eye movement data, at least one of (i) bad tracking of the target by the subject and (ii) no tracking of the target by the subject during a plurality of time intervals, wherein each of the plurality of time intervals corresponds to a respective one of the plurality of stimuli,
    (d) receive, from the one or more sensors, the data indicative of pupil size of at least one eye of the subject, wherein the data includes a plurality of segments, and wherein each of the plurality of segments corresponds to a respective one of the plurality of stimuli,
    (e) derive, based on the pupil size data, at least one parameter that corresponds to each of the plurality of segments,
    (f) determine a probability that the subject is being deceptive in response to a given one of the plurality of stimuli based on a combination of (a) whether bad tracking or no tracking was determined for the time interval that corresponds to the given stimulus and (b) the at least one parameter derived from the segment of data that corresponds to the given stimulus, and
    (g) produce an output signal indicative of the determined probability.

12. The system of claim 11, wherein the processor is further configured to apply one or more counter measure algorithms using the at least one eye dynamic signal to detect deception.

13. The system of claim 11, wherein the processor is further configured to expose the subject to a relaxing element.

14. The system of claim 11, wherein the processor is further configured to determine an optimal timing for exposing the subject to a stimulus from the stimuli sequence based on physiological activity and/or behavior indicators of the subject.

15. The system of claim 14, wherein the physiological activity of the subject comprises: eye dynamics, GSR, heart rate, respiration, body temperature, blood pressure, or any combination thereof.

16. The system of claim 11, wherein the at least one evoking stimulus comprises displaying an image to the subject.

17. The system of claim 11, wherein the at least one evoking stimulus comprises asking the subject a question.

18. The system of claim 11, wherein the at least one evoking stimulus comprises displaying an image to the subject and asking the subject a corresponding question.

19. The system of claim 11, wherein the at least one parameter that corresponds to each of the plurality of segments comprises an integral of the pupil size data for the respective segment.

20. The system of claim 11, wherein the at least one parameter that corresponds to each of the plurality of segments comprises (a) an integral of the pupil size data for each of the plurality of segments and (b) a peak of the pupil size data for each of the plurality of segments.

* * * * *